United States Patent
Nip

(10) Patent No.: US 8,258,180 B2
(45) Date of Patent: Sep. 4, 2012

(54) METHODS FOR MAKING ORGANOZINC SALTS AND COMPOSITIONS CONTAINING THE SAME

(76) Inventor: Raymond L. Nip, Bangkok (TH)

( * ) Notice: Subject to any disclaimer, the term of this patent is extended or adjusted under 35 U.S.C. 154(b) by 494 days.

(21) Appl. No.: 12/346,535

(22) Filed: Dec. 30, 2008

(65) Prior Publication Data

US 2010/0168230 A1 Jul. 1, 2010

(51) Int. Cl.
*A01N 55/02* (2006.01)
*A01N 37/00* (2006.01)
*A61K 31/19* (2006.01)

(52) U.S. Cl. .......................... 514/494; 514/557; 514/558
(58) Field of Classification Search .................. None
See application file for complete search history.

(56) References Cited

U.S. PATENT DOCUMENTS

| | | |
|---|---|---|
| 2,492,314 A | 12/1949 | Olin et al. |
| 2,690,448 A | 9/1954 | Luginbuhl |
| 3,637,788 A | 1/1972 | Werth et al. |
| 3,674,824 A | 7/1972 | Amidon et al. |
| 3,678,135 A | 7/1972 | Mastromatteo et al. |
| 3,725,443 A | 4/1973 | Horiie et al. |
| 3,992,548 A | 11/1976 | Pommer et al. |
| 4,060,535 A | 11/1977 | Cinco |
| 4,060,624 A | 11/1977 | Klopping |
| 4,071,357 A | 1/1978 | Peters |
| 4,207,377 A | 6/1980 | Kindrick |
| 4,517,336 A | 5/1985 | Wolff et al. |
| 4,831,171 A | 5/1989 | Bergfeld et al. |
| 5,188,663 A | 2/1993 | Ikari et al. |
| 5,204,084 A | 4/1993 | Robinson et al. |
| 5,274,144 A * | 12/1993 | Wuest et al. ................... 554/156 |
| 5,302,315 A | 4/1994 | Umland |
| 5,314,719 A | 5/1994 | Batdorf et al. |
| 5,610,240 A | 3/1997 | Hogt et al. |
| 5,623,007 A | 4/1997 | Kuebler |
| 5,643,852 A | 7/1997 | Lucas et al. |
| 5,872,188 A | 2/1999 | Datta et al. |
| 6,004,570 A | 12/1999 | Kostansek |
| 6,079,468 A | 6/2000 | D'Sidocky et al. |
| 6,291,572 B1 | 9/2001 | Brown et al. |
| 6,333,375 B1 | 12/2001 | Nakamura et al. |
| 6,436,421 B1 | 8/2002 | Schindler et al. |
| 6,534,675 B2 | 3/2003 | Schubart et al. |
| 6,555,075 B2 | 4/2003 | Nip |
| 2003/0152508 A1 | 8/2003 | Nip |
| 2006/0281009 A1 | 12/2006 | Boyer et al. |
| 2007/0072959 A1 * | 3/2007 | Nip ............................... 523/200 |
| 2008/0161475 A1 | 7/2008 | York et al. |
| 2008/0194748 A1 | 8/2008 | Futamura |

FOREIGN PATENT DOCUMENTS

WO 2007041060 A1 4/2007

OTHER PUBLICATIONS

"Electric Arc Furnace Dust"; http://www.recupac.com/eaf_dust.htm.
Raymond L. Nip; "Zinc Oxide Coated Particles, Compositions Containing the Same, and Methods for Making the Same"; U.S. Appl. No. 11/519,949, filed Sep. 11, 2006.
Susan Budavari, Maryadele J. O'Neil, Ann Smith, Patricia E. Heckelman and Joanne F. Kinneary; "The Merick Index—An Encyclopedia of Chemicals, Drugs, and Biologicals"; pp. 1344 and 1736-1737; 12th Edition; Merck Research Laboratories a Division of Merck and Co., Inc.
International Search Report and Written Opinion; International Application No. PCT/US 09/69610; Dated Mar. 10, 2010; 7 pages; International Searching Authority/United States, Commissioner for Patents, Alexandria, Virginia.

* cited by examiner

*Primary Examiner* — Johann Richter
*Assistant Examiner* — James Meadows
(74) *Attorney, Agent, or Firm* — The Law Offices of Andrew D. Fortney; Andrew D. Fortney

(57) ABSTRACT

Organic zinc salts and mixtures thereof, organic zinc salt coated particles, methods of preparing organic zinc salts and organic zinc salt coated particles, and various applications of such coated particles, including applications in rubber, other polymeric materials, and pesticides and/or fungicides are disclosed.

33 Claims, No Drawings

METHODS FOR MAKING ORGANOZINC SALTS AND COMPOSITIONS CONTAINING THE SAME

FIELD OF THE INVENTION

The present invention generally relates to the field of organic zinc salts, methods of making organic zinc salts, organic zinc salt coated particles, and various applications of such organic zinc salts and organic zinc salt coated particles, including applications in rubber and other polymer materials and the like, in which the organic zinc salts and organic zinc salt coated particles function, e.g., as one or more of an anti-reversion agent, a vulcanization activator and/or accelerator, a rheology modifying agent, and/or a filler for rubber or plastics (especially in tires). Organic zinc salts of the present invention may also be used as fungicides and/or pesticides.

DISCUSSION OF THE BACKGROUND

Organic zinc salts are used in rubber compounding (e.g., in the manufacture of tires). When a rubber product is mixed and formed (e.g., in a mold), it is typically heated in a curing process (i.e., for a length of time and/or at a temperature sufficient to effect such curing). Careful control of process conditions in such a curing process is essential to impart one or more desired characteristics to a cured rubber product. However, in the case of large and/or thick rubber products, heat transfer to the rubber product during a curing may be non-uniform throughout the rubber material due to the heat transfer characteristics of the material being cured (i.e., longer times are necessary for heat transfer to the bulk material from the surface of a mold). This may result in an uneven curing process (e.g., over-cured surface regions relative to the bulk material), yielding a product with undesirable characteristics resulting from such over-curing at a surface of a rubber product, a phenomenon commonly referred to as reversion. Such an over-cured surface region may have a lower hardness, elastic modulus, abrasion resistance, etc.

There are a number of additives available to reduce the occurrence and/or mitigate the extent of reversion in the curing of rubber products. U.S. Pat. Nos. 5,302,315, 5,610,240, 5,623,007 and 5,872,188 (the relevant portions of each of which are incorporated herein by reference) all address either the preparation or use of such anti-reversion agents. Such anti-reversion agents may comprise a mixture of organic zinc salts (also known as organic zinc soaps) prepared from $C_7$-$C_{24}$ fatty acid and zinc salts of aromatic carboxylic acids such as benzoic acid, chlorobenzoic acid, and/or methylbenzoic acid. Together with conventional organic zinc salts such as zinc stearate, zinc laurate, and zinc oleate, these organic zinc salts have large markets and varied applications in the rubber, plastics and cosmetics industries.

One method for preparing such organic zinc salts is referred to as a fusion method. In a fusion method for preparing such organic zinc salts, a zinc compound such as zinc oxide, zinc hydroxide, and/or zinc carbonate is heated in the presence of an organic acid such as stearic acid, oleic acid, and/or other organic acid to yield the corresponding organic zinc salt. Organic zinc salts formed via such a fusion method have a higher bulk density and a larger volume-to-mass (V/m) ratio relative to organic zinc salts prepared via other methods.

A second method for preparing such organic zinc salts employs the reaction between a sodium, ammonium or potassium salt of one or more organic acids and zinc sulfate, zinc acetate and/or zinc chloride. The product of such a method may be precipitated out of an aqueous reaction medium, and washed with water to remove byproducts such as sodium sulfate, sodium chloride, ammonium sulfate, etc., and then dried. Organic zinc salts produced by this second method are typically referred to as precipitated organic zinc salts, and are considered superior relative to similar salts produced via the fusion method previously described.

However, this second organic zinc salt production methodology requires additional process steps and/or chemical reagents relative to a fusion method to effect the desired transformation, resulting in an increased cost. This second method also produces additional waste in the form of byproducts such as sodium sulfate, ammonium sulfate, and/or sodium chloride. Such sodium sulfate, ammonium sulfate, and/or sodium chloride byproducts are often in such a dilute state after washing a product organic zinc salt that it is not economical to recover such byproducts, and the filtrate is discarded. Disposal of such filtrate (with dissolved byproducts therein) has potentially negative environmental consequences via an increase in the level of water soluble salts in the environment.

A third method of making organic zinc salts comprising dithiocarbamates is described in U.S. Pat. No. 2,492,314 (the relevant portions of which are incorporated herein by reference). An amine, carbon disulfide, and zinc oxide are employed to produce organic zinc salts under anhydrous conditions. However, the resulting product has less than desirable properties, including relatively coarse, large particles. Thus, the preferred method for producing organic zinc salts has been the second method described above, from water soluble zinc salts like zinc chloride, and/or zinc acetate, and more preferably, zinc sulfate, as described in U.S. Pat. No. 6,534,675 (the relevant portions of which are incorporated herein by reference).

It is known that zinc-ammonia-carbonate complexes and solutions thereof may used to produce active zinc oxide and/or zinc carbonate (see, e.g., U.S. Pat. No. 6,555,075, the relevant portions of which are incorporated herein by reference). The active zinc oxide or zinc carbonate produced thereby is then further reacted with one or more organic acids to make the corresponding organic zinc salts. This present invention improves upon the processes described above, providing methods whereby organic zinc salts may be obtained directly from a zinc-ammonia-carbonate complex and/or a solution thereof, obviating the need for a dedicated step to generate an active zinc oxide and/or zinc carbonate. The organic zinc salts afforded by the present methods may also possess superior characteristics relative to organic zinc salts produced by the fusion method described above.

Organic salts may also used to coat siliceous particles like precipitated silica, clay, kaolin, talc, aluminum silicate, calcium carbonate, carbon black and mixtures thereof. Such coated particles, when added to rubber compositions as fillers, impart advantageous characteristics to rubber products formed therefrom, including improved abrasion resistance, modulus, and tensile strength (see, e.g., U.S. Pat. Appl. Publ. Nos. 2006/0281009, 2008/0194748, and 2008/0161475, and U.S. Pat. Nos. 6,291,572 and 6,333,375, the relevant portions of each of which are incorporated herein by reference).

Organic zinc salts and organic zinc salt coated fillers may improve the Mooney viscosity, modulus, hardness and abrasion resistance of a rubber compound compared with untreated fillers. Reducing the Mooney viscosity results in a more facile processing of a rubber compounding composition containing organic zinc salts and/or organic zinc salt coated fillers. This improvement is important for tires. An organic zinc salt coating can be formed on siliceous fillers when such fillers are first precipitated from solution, before drying, obviating a need for multiple drying steps. Of course, the zinc salts or mixture of zinc salts of this invention can be added separately with siliceous fillers, rubber processing aids such as accelerators, sulfur, antioxidants, processing oils, etc., with or without silane in rubber recipes to obtain the desired properties as the treated fillers above.

SUMMARY OF THE INVENTION

Embodiments of the present invention relate to methods of producing organic zinc salts, methods of making organic zinc salt coated particles, and applications thereof. The organic zinc salts and organic zinc salt coated particles may have many applications in rubber products, such as shoe soles, rubber bands, tires, and the like, and other polymer products. The organic zinc salts may function as one or more of an anti-reversion agent, a rheology modifying agent, a coating for a filler material, and an activator for vulcanization or other reaction. The organic zinc salts described herein may also function as pesticides and/or fungicides.

In some embodiments, the present invention provides methods for the synthesis of organic zinc salts via the generation of a zinc ammonia complex, and subsequent treatment of such a complex with one or more organic acids and/or salts thereof to form the organic zinc salts. Such methods avoid the formation of sodium chloride and/or sodium sulfate byproducts as in the conventional methods described above, byproducts whose value does not warrant recovery. Conversely, the use of sodium hydroxide, ammonia and carbon dioxide in some embodiments of the present invention yields a sodium hydroxide/sodium carbonate byproduct mixture. Such a byproduct mixture has a higher value relative to the sodium chloride or sodium sulfate byproducts produced by conventional methods, and recovery of these byproducts is economically advantageous. Thus, the present methods provide a method of producing organic zinc salts where value-added byproducts are produced.

In some embodiments, ammonia is used to form ammonium salts of an organic acid or acids in the preparation of organic zinc salts. Most or substantially all of the ammonia from such ammonium salts employed in such a process may be evaporated and recovered. Consequently, organic zinc salts produced by such a method may be free from water soluble matter, reducing the amount of water required for washing of a product, or, or eliminating the need to wash a product altogether. Such a method reduces the quantity of water required for such a washing process and/or the volume of filtrate therefrom that must be disposed or discharged. Therefore the present methods provide an environmentally friendly alternative to conventional methods for the production of organic zinc salts.

In some embodiments, organic zinc salts may be used to coat siliceous fillers such precipitated silica, clay, aluminum silicate, and mixture thereof. Such organic zinc coated fillers may impart improved abrasion resistance, modulus, or tensile strength to rubber products containing such coated fillers (see, e.g., U.S. Pat. Appl. Nos. 2006/0281009, 2008/0194748, 2008/0161475 and U.S. Pat. Nos. 6,291,572 and 6,333,375). By precipitating organic zinc salts and/or mixtures of organic zinc salts on fillers like precipitated silica, clay, talc, calcium carbonate, carbon black etc., the organic zinc salt coating may also serve as a coupling agent, reducing or eliminating the need for added silane coupling agents in a rubber compound. In addition, organic zinc salts, organic zinc salt coated particles, silane coupling agents, and processing aids such as accelerators, sulfur, antioxidants, processing oils, etc., may be used in various combinations to improve the properties of a rubber compound containing such combinations relative to an otherwise identical rubber compound containing a silane coupling agent alone. Incorporation and dispersion of organic zinc coated fillers in a rubber compound or a plastic formulation may also be improved.

Such coated filler may also improve one or more properties (e.g., Mooney viscosity, elastic modulus, hardness, abrasion resistance, etc.) of a rubber compound containing such coated particles relative to an otherwise identical rubber compound containing uncoated particles. For example, an improved Mooney viscosity may result in improved processing characteristics of a rubber compound mixture, and such improvements are particularly beneficial in the production of tires.

In some embodiments, organic zinc salts or mixtures thereof provided by the present methods may be added to a rubber compounding mixture either alone, or in combination with siliceous fillers with or without silane coupling agents in rubber recipes to obtain desired properties imparted by the organic zinc coated fillers described above. This may be particularly advantageous for fillers comprising clays or kaolin, which typically have larger particle sizes than precipitated silica. Of course, organic zinc salts or mixtures thereof may be added to a rubber compounding composition with uncoated siliceous fillers, with or without silane coupling agents, to obtain desired properties similar to those obtained with rubber compounds comprising organic zinc salt coated fillers. This may be especially true for clay or kaolin fillers, which typically have larger particle sizes relative to precipitated silica filler particles.

The present invention also offers the opportunity to make products, e.g., rubber products, with improved abrasion resistance. For example, clays (especially surface modified clay with silane coupling agents) are increasingly being used in tires and other rubber compounds. Silanes and clays generally increase the modulus and reduce heat build up of the rubber compound so that rolling resistance of tires is decreased and fuel savings are realized. An organic zinc salt coating on a substrate particle, especially an inorganic or platy particle such as a clay, should provide at least part of the performance of the silane coupling agent for the rubber compound, and with improved abrasion resistance. Indeed, an organic zinc salt coated particle often increases the abrasion resistance compared with clay and zinc oxide added separately. With or without the silane coupling agent, organic zinc salt coated clays may increase the modulus at 100% and/or 300% elongation and may reduce heat-build up in rubber compounds. This indicates that the rolling resistance of tires can be decreased. The organic zinc salt-coated particle can thus be used as a partial carbon black or silica substitute. Thus, one particle can serve multiple functions, simplifying formulation and processing.

These and other advantages of the present invention will become readily apparent from the detailed description of preferred embodiments below.

DETAILED DESCRIPTION

Reference will now be made in detail to various embodiments of the invention. While the invention will be described in conjunction with the disclosed embodiments, it will be understood that they are not intended to limit the invention. On the contrary, the invention is intended to cover alternatives, modifications and equivalents that may be included within the spirit and scope of the invention as defined by the appended claims. Furthermore, in the following detailed description of the present invention, numerous specific details are set forth in order to provide a thorough understanding of the present invention. However, it will be readily apparent that the present invention may be practiced without these specific details. In other instances, well-known methods, procedures, components, and circuits have not been described in detail so as not to unnecessarily obscure aspects of the present invention.

The invention, in its various aspects, will be explained in greater detail below with regard to exemplary embodiments.

In one preferred method for preparing organic zinc salts, a zinc containing solution is prepared. The zinc containing solution is generally basic. Most conveniently, it is obtained by dissolving zinc oxide and/or other zinc bearing materials like zinc carbonate, roasted zinc sulfide ore, etc., in an aqueous solution comprising an ammonia source (e.g., ammonia gas) and (optionally) a carbon dioxide source (e.g., carbon dioxide) to form a zinc ammonia carbonate complex (Zn[$NH_3$]$_4CO_3$) solution (see, e.g., co-pending U.S. patent application Ser. No. 11/519,949, filed Sep. 11, 2006, the relevant portions of which are incorporated herein by reference). In some embodiments (e.g., when zinc oxide and/or zinc carbonate is used as the zinc bearing material), the introduction of carbon dioxide is not required. Lower grade zinc bearing materials like zinc ash, electric arc furnace (EAF) dust, or other waste zinc materials can be substituted, but purification of the zinc ammonia carbonate complex solution may then be desirable. Purification can be easily accomplished according to U.S. Pat. No. 5,204,084 (the relevant portions of which are incorporated herein by reference).

The weight percent of ammonia in the zinc ammonia carbonate complex solution can be from 1% to about 20%. The amount of zinc dissolved in the solution may be (and preferably is) from 1 to 15% by weight. The weight percent of carbon dioxide in the solution can be from 0% to about 10%. If low heavy metal and/or low iron content is desired, the solution optionally can be purified according to U.S. Pat. No. 4,207,377 (the relevant portions of which are incorporated herein by reference. Such a purification process enables the use of lower grade of zinc bearing materials like zinc ash, EAF dust, or other waste zinc materials. The solution desirably is then filtered. If further purification is desired, it may be done according to U.S. Pat. No. 4,071,357 (the relevant portions of which are incorporated herein by reference). The zinc ammonia carbonate complex solution desirably is formed at a temperature in the range of from about 20° C. to about 60° C. Any suitable pressure may be used, but atmospheric pressure often is most convenient.

An organic acid or a mixture of organic acids is then added to the zinc ammonia carbonate complex solution. Examples of organic acids that may be used include aliphatic carboxylic acids (e.g., resinic acid, $C_7$-$C_{24}$ aliphatic carboxylic acids such as stearic acid, lauric acid or other fatty acids), aromatic carboxylic acids (e.g., benzoic acid, chlorobenzoic acid and methylbenzoic acid), 2-mercaptobenzothiazole, N,N-disubstituted dithiocarbamic acids such as N,N-di($C_1$-$C_4$ alkyl) dithiocarbamic acids (e.g., N,N-dimethydithiocarbamic acid, N,N-diethyldithiocarbamic acid, N,N-dibutyldithiocarbamic acid) N,N-di($C_6$-$C_{10}$ aryl)carbamic acids and N,N-di($C_6$-$C_{10}$ aralkyl)carbamic acids (e.g., N,N-dibenzylcarbamic acid), $C_2$-$C_6$ alkylenebisdithiocarbamic acids (e.g., ethylenebisdithiocarbamic acid), and mixtures thereof (e.g., a mixture of alkyl and aryl carboxylic acids). The organic acid(s) and the zinc of the zinc ammonia complex may be present in a molar ratio of from about 0.8:1 to 2.2:1.

In an alternative embodiment, a solution of an alkali salt of the organic acid (or acids) is prepared, then added to the zinc ammonia carbonate complex solution. The organic acid is added to an aqueous solution comprising an alkaline compound such as ammonium hydroxide, or an alkali metal hydroxide such as sodium hydroxide or potassium hydroxide, to form an alkali salt of the organic acid or acids. This acid salt solution is then added to the zinc ammonia complex solution described above, and agitated.

The mixture comprising the organic acid(s) or salt(s) thereof and the zinc ammonia complex may then be heated to liberate most or substantially all of the ammonia and carbon dioxide (if present). Heating is preferably conducted at a temperature of from about 50° C. to about 150° C. If desired, the mixture may then be cooled to a temperature of from about 5° C. to about 30° C. to further promote the precipitation of the organic zinc salt products. The organic zinc salt is then isolated by, e.g., filtration. If desired, the isolated salts may be washed with water to remove any water soluble byproducts present in the precipitate. The precipitate may then be dried, preferably at a temperature of from about 50° C. to about 200° C. If desired, the organic zinc salt product may be milled to a powder.

In a preferred embodiment for forming organic zinc salts of substituted dithiocarbamates, a (di)substituted amine is selected to afford the desired substituent(s) on the zinc (substituted) dithiocarbamate salt product. For example, diethylamine (and carbon disulfide) afford zinc diethyldithiocarbamate. In a typical procedure, an amine is dissolved in water, and then a solution of ammonium hydroxide is added to the aqueous amine solution with vigorous stirring, maintaining the solution at ambient temperature (e.g., a temperature of about 25° C.). If desired, an emulsifier (e.g., Tanemul 1203) may be added. Carbon disulfide is then added to the mixture with vigorous stirring. The mixture is maintained at a temperature of less than about 40° C. (preferably ≦20° C.) during the addition of carbon disulfide. The zinc ammonia carbonate complex solution described above is then added, and most of the zinc salt precipitates. The mixture may then be heated to liberate most or substantially all of the ammonia and carbon dioxide (if present). Heating is preferably conducted at a temperature of from about 50° C. to about 150° C. During heating, more organic zinc salts precipitate. If desired, the mixture may then be cooled to a temperature of from about 5° C. to about 30° C. to further promote the precipitation of the organic zinc salt products. The organic zinc salt is then isolated by, e.g., filtration. If desired, the isolated salts may be further washed with water to remove any water soluble byproducts present in the precipitate. The precipitate may then be dried, preferably at a temperature of from about 50° C. to about 200° C. If desired, the product organic zinc salt may be milled to a powder.

In an alternative embodiment for forming organic zinc salts of substituted dithiocarbamates, the zinc ammonia complex may be generated in situ. An amine (e.g., diethylamine) is dissolved in water, and a solution of ammonium hydroxide is then added to the aqueous amine solution with vigorous stirring, maintaining the solution at a temperature of about 25° C. Zinc oxide, carbon dioxide, and ammonia are then added to this solution, generating the zinc ammonia carbonate complex in situ. If desired, an emulsifier (e.g., Tanemul 1203) may be added. Carbon disulfide is then added to the mixture with vigorous stirring. The mixture is maintained at a temperature of less than about 40° C. (preferably ≦20° C.) during the addition of carbon disulfide, and the organic zinc salt(s) precipitate. The mixture may then be heated to liberate most or substantially all of the ammonia and carbon dioxide (if present). Heating is preferably conducted at a temperature of from about 50° C. to about 150° C. During heating, additional organic zinc salt(s) may precipitate. If desired, the mixture may then be cooled to a temperature of from about 5° C. to about 30° C. to further promote the precipitation of the organic zinc salt products. The organic zinc salt is then isolated by, e.g., filtration. If desired, the isolated salts may be further washed with water to remove any water soluble byproducts present in the precipitate. The precipitate may then be dried, preferably at a temperature of from about 50° C. to about 200° C., removing any remaining ammonia and/or carbon dioxide. If desired, the organic zinc salt product may be milled to a powder.

In another alternate embodiment for forming organic zinc salts of substituted dithiocarbamates, the order of addition of zinc ammonia complex and carbon disulfide is reversed. As described previously, an amine is dissolved in water, and a solution of ammonium hydroxide is then added to the aqueous amine solution with vigorous stirring, maintaining the solution at a temperature of about 25° C. The previously described zinc ammonia carbonate complex (or solution thereof) is then added. If desired, an emulsifier (e.g., Tanemul 1203) may be added. Carbon disulfide is then added to the mixture with vigorous stirring. The mixture is maintained at a temperature of less than about 40° C. (preferably ≦20° C.) during the addition of carbon disulfide, and the organic zinc salt(s) precipitate. The mixture may then be heated to liberate most or substantially all of the ammonia and carbon dioxide (if present). Heating is preferably conducted at a temperature of from about 50° C. to about 150° C. During heating, more organic zinc salt(s) may precipitate. If desired, the mixture may then be cooled to a temperature of from about 5° C. to about 30° C. to further promote the precipitation of the organic zinc salt products. The organic zinc salt is then isolated by, e.g., filtration. If desired, the isolated salts may be further washed with water to remove any water soluble byproducts present in the precipitate. The precipitate may then be dried, preferably at a temperature of from about 100° C. to about 200° C. If desired, the organic zinc salt product may be milled to a powder.

In another embodiment of the present invention, organic zinc salt-coated composite particles may be prepared. In this embodiment, a coating comprising one or more organic zinc salts may be formed on one or more types of inorganic substrate particles. The zinc material may be precipitated onto the substrate particles from an admixture derived from ingredients comprising the previously described zinc ammonia carbonate complex, one or more organic acids and/or salts thereof, and the substrate particles. Suitable inorganic substrates include silica, clay, kaolin, talc, aluminum silicate, calcium carbonate, carbon black and mixtures thereof. The resultant suspension comprising the organic acid(s) or salt(s) thereof, the zinc ammonia carbonate complex and the substrate particles may then be heated to liberate most or substantially all of the ammonia and carbon dioxide (if present). Heating is preferably conducted at a temperature of from about 50° C. to about 150° C. During heating, the organic zinc salts precipitate onto the filler material particles, forming the organic zinc salt coated composite particles. The relative proportions of zinc ammonia complex, organic acid(s) or salt(s) thereof and filler particles are chose such that the coating on the filler particles is present in an amount of from 1 to 30 wt. % of the coated particle.

If desired, the mixture may then be cooled to a temperature of from about 5° C. to about 50° C. to further promote the precipitation of the organic zinc salt(s) on the filler particles. The organic zinc salt coated particles are then isolated by, e.g., filtration. If desired, the isolated organic zinc coated particles may be further washed with water to remove any water soluble byproducts present. The organic zinc salt coated may then be dried, preferably at a temperature of from about 100° C. to about 200° C. If desired, the product organic zinc salt coated particles may be milled to a powder.

In a preferred embodiment, the solution of the zinc ammonia complex and the organic acids(s) or alkaline salt(s) thereof may be sprayed onto the onto the filler material particles. The solution covered particles may then be agitated and heated to liberate most or substantially all of the ammonia and carbon dioxide (if present). Heating is preferably conducted at a temperature of from about 50° C. to about 150° C. During heating, the organic zinc salts precipitate onto the filler material particles, forming the organic zinc salt coated composite particles. The relative proportions of zinc ammonia carbonate complex, organic acid(s) or salt(s) thereof and filler particles are chosen such that the coating on the filler particles is present in an amount of from 1 to 30 wt. % of the coated particle.

Certain of the present zinc salts of organic acids can be used as fungicides and/or pesticides. For example, zinc dimethyldithiocarbamate and zinc ethylenebisdithiocarbamate are useful as fungicides and/or pesticides (see, e.g., U.S. Pat. Nos. 6,436,421, 5,643,852, 5,314,719, 5,188,663, 4,060,624, and 3,992,548, the relevant portions of which are incorporated herein by reference).

The following examples will further illustrate the present invention.

EXAMPLES

For the following examples, materials are obtained from the following sources:
  Zinc oxide white seal—Univenture Public Company Ltd., Bangkok
  Stearic acid—Imperial Industrial Chemicals, Bangkok
  Zinc 2-mercaptobenzothiazole—Master Glove Co. Ltd., Thailand
  2-Mercaptobenzothiazole—Nguan Soon Huat Co. Ltd., Thailand
  Benzoic acid—American International Chemical, Inc. USA
  Blends of caprylic/capric acid—Imperial Industrial Chemicals, Bangkok
  Aromatic oil—Nguan Soon Huat Co. Ltd., Thailand
  Anti oxidant 6 PPD—Flexsys NV, Belgium
  Antireversion agent Perkalink 900—Flexsys NV, Belgium
  Precipitated silica VN3—Degussa AG, Germany
  Clay 5400—Lorwattana Co. Ltd., Thailand
  Accelerator TBBS—Nguan Soon Huat Co. Ltd., Thailand
  Accelerator TMTD—Nguan Soon Huat Co. Ltd., Thailand
  Accelerator MBTS—Nguan Soon Huat Co. Ltd., Thailand
  Accelerator ZMBT—Master Glove Co. Ltd., Thailand
  Accelerator ZDEC—Qingdao Brisk Chemical Co. Ltd., China
  Silane Si69—Degussa AG, Germany
  Emulsifier Tanemul 1203—Tanatex Chemicals, Germany
  Testing methods and equipment include:
  Cure characteristics—ASTM D2084, Oscillating Disk Rheometer, Monsanto
  Mooney viscosity—ASTM 1646
  Sample Curing—compression moulding
  Hardness—ASTM D2240
  Tensile & modulus—ASTM D 412
  Heat buildup—ASTM D623
  Rubber Process Analyzer (RPA 2000, Alpha Technology) for G' (Elastic modulus) and Tan delta (ratio of viscous modulus to elastic modulus)
  Abrasion—DIN 53 516

Reversion—DIN 53 529

Acid Value—Add 1.000 gram of sample to 20 ml of ethanol and heat up to 65 C until it dissolves. Titrate the solution with 0.25 N NaOH solution with phenolphthalin indicator until clear or weak pink color. Calculate as: Acid value in mg of KOH per gram of sample=(volume of 0.25N NaOH)×0.25×56.1

Example 1

Preparation of Zinc Stearate

Bubble 63 grams of ammonia gas and 29 grams of carbon dioxide gas into 386 grams of water, then add 65 grams of zinc oxide into the solution. Stir well and the zinc oxide completely dissolves into the solution. Analysis shows that the solution contains 9.56 wt. % zinc with a pH of 11.56. This solution is called solution A. 450 grams of stearic acid is added to solution A and stirred well. The stearic acid completely dissolves in the solution. Heat the solution in a laboratory reactor with agitation and a water cooled condenser to recover the evaporated ammonia and carbon dioxide. The solution boils at around 65° C. and as it is boiling, white gelatinous precipitates form. As water level drops, 1,500 ml more of water is added to the mixture. When most of the ammonia is boiled out the temperature rises to 100° C. and the pH drops to 9.27. Cool the mixture to 25° C. to precipitate other slightly soluble organic zinc salts which may be in the solution, then filter and predry the white precipitate at 90° C. for 2 hours to remove most of the water. Then further dry the precipitate at 105° C. for one hour, and mill it to obtain zinc stearate A.

Using the conventional fusion method, zinc stearate B was prepared. Following are properties of both samples:

|  | Zinc Stearate A | Zinc Stearate B |
| --- | --- | --- |
| Zinc (wt. %) | 10.17 | 10.22 |
| Acid Value (mg KOH/g) | 18.43 | 96 |
| Melting point (° C.) | 112 | 116 |
| pH | 8.09 | 6.35 |
| Bulk density (g/cm$^3$) | 0.36 | 0.45 |

Other water insoluble or sparingly soluble organic zinc salts or mixtures of organic zinc salts like zinc resinate, zinc laurate, zinc oleate, and zinc salts of coconut fatty acids can also be made according to the method described for the preparation of zinc stearate A.

Example 2

Preparation of Zinc 2-Mercaptobenzothiazole (ZMBT)

Prepare 600 grams of solution A as in Example 1 with 9.56% zinc. Add 243 grams of 2-mercaptobenzothiazole with acid value of 327 mg of KOH per gram and melting point of about 180° C. to the solution. Stir and warm the solution to 50° C. for one hour. The pH of this solution is measured at 10.67. Heat the solution to boil off the ammonia and carbon dioxide. The solution boils at about 60° C. to 90° C. When all the ammonia is boiled out the temperature rises to 100° C. and the pH drops to 8.57. Cool the mixture to 25° C. Filter the mixture and dry the white precipitate at 150° C. for 6 hours, and then and mill it to obtain zinc 2-mercaptobenzothiazole (ZMBT), sample No. ZMBT-A, with the following properties:

|  | ZMBT A | Commercial ZMBT |
| --- | --- | --- |
| Zinc (wt. %) | 18.56 | 17.42 |
| Acid Value (mg KOH/g) | 52.07 | 50 |
| Melting point (° C.) | 330 (dec) | 330 (dec) |
| pH | 7.57 | 7.88 |
| Bulk density (g/cm$^3$) | 0.58 | 0.6 |
| Residue on 150 Mesh Sieve (wt. %) | 0.1 | 2.4 |

This material has comparable characteristics to commercial zinc 2-mercaptobenzothiazole obtained from Master Glove (commercial ZMBT).

Example 3

Alternative Preparation of Zinc 2-Mercaptobenzothiazole

Prepare 340 grams of solution A as in Example 1 with 9.56% zinc. Dissolve 168 grams of 2-mercaptobenzothiazole with melting point of about 180° C. in a solution with 40.4 grams of sodium hydroxide diluted to 805 ml of aqueous solution. The pH of the solution is measured to be 10.88. Mix the two solutions and stir vigorously. The pH of the mixture is measured at 10.92. Ammonia is liberated and white precipitates appear. Filter and wash the precipitates until the pH of the washing water drops to 9.55. Dry the white precipitates at 160° C. for 5 hours and then and mill it to obtain zinc 2-mercaptobenzothiazole, sample No. ZMBT-B, with the following properties:

|  | ZMBT B | Commercial ZMBT |
| --- | --- | --- |
| Zinc (wt. %) | 17.58 | 17.42 |
| Acid Value (mg KOH/g) | 36.8 | 50 |
| Melting point (° C.) | 330 (dec) | 330 (dec) |
| pH* | 7.25 | 7.88 |
| Bulk density (g/cm$^3$) | 0.48 | 0.6 |
| Residue on 150 Mesh Sieve (wt. %) | 0.5 | 2.4 |

*5 grams in 500 ml distilled water

This method requires one more chemical then the previous method described in Example 2 above (i.e., sodium hydroxide). However, the sodium hydroxide can be recovered and reused easily. The sodium hydroxide and/or sodium carbonate recovered has much higher commercial value than sodium chloride and/or sodium sulfate produced as byproducts in conventional methods. No acid is consumed in this process.

Using commercial sodium diethyldithiocarbamate dissolved in aqueous solution and zinc ammonia carbonate complex solution, zinc diethyldithiocarbamate can be readily precipitated in the same manner. However, unlike zinc diethyldithiocarbamate, which can be precipitated from ammonium diethyldithiocarbamate, it is not practical to precipitate zinc 2-mercaptobenzothiazole from its ammonium salt as the solubility of 2-mercaptobenzothiazole in ammonia is very low.

Example 4

Preparation of Mixed Organic zinc Salts From Aliphatic and Aromatic Carboxylic Acids Prepare 400 grams of solution A as in Example 1 with 9.56% zinc. Add 42.8 grams of benzoic acid into 128 grams of caprylic/capric acid blend. Stir until the benzoic acid completely dissolves in the caprylic/capric acid blend. Mix both solutions together and they completely dissolve into each other. Heat the solution in a laboratory reactor with agitation and a water cooled condenser to recover the evaporated ammonia and carbon dioxide. The solution boils at 80° C. and precipitates appear as the temperature rises over 90° C. When most of the ammonia is boiled out the pH drops to 7.89. Cool the mixture to 4° C. to precipitate other slightly soluble organic zinc salts which may be in the solution, then filter and dry the yellowish precipitates at 140° C. for three hours. The precipitate melts during the drying process. Let the melt cool down and grind it to obtain mixture of zinc salts of benzoic acid and capric/caprylic acid Sample No. Mixed-Zn-A. Using the method described in U.S. Pat. No. 5,302,315, we prepare the mixed organic zinc_salt sample Mixed-Zn-B as comparative example. The sample properties are listed below:

|  | Mixed Zn-A | Mixed Zn-B |
|---|---|---|
| Zinc (wt. %) | 17.57 | 18.45 |
| Softening point (° C.) | 60 | 92 |
| Melting point (° C.) | 65 | 95 |
| Appearance | Rubber-like | Hard/brittle |

Other acids like 2-methylbenzoic acid or 2-chlorobenzoic acid can also be used in place of benzoic acid for the manufacture of the organic zinc salt anti reversion agent.

Example 5

Use of Mixed Organic Zinc Salts From Aliphatic and Aromatic Carboxylic Acids as an Anti-Reversion Agent in a Rubber Compound Tire tread made of natural rubber is compounded according to the following recipes. All units are in phr (parts per hundred parts of rubber).

| | Test No. | | | | |
|---|---|---|---|---|---|
| | T1 | T2 | T3 | T4 | T5 |
| | Anti Reversion Agent | | | | |
| | Mixed-Zn-A | Mixed-Zn-B | None | PK900 | PK900 + Mixed-Zn-A |
| Natural Rubber | 100 | 100 | 100 | 100 | 100 |
| Carbon Black N330 | 48.5 | 48.5 | 48.5 | 48.5 | 48.5 |
| Aromatic Oil | 8 | 8 | 8 | 8 | 8 |
| Stearic Acid | 2 | 2 | 2 | 2 | 2 |
| Anti oxidant Santo flex 6PPD | 1 | 1 | 1 | 1 | 1 |
| Anti Reversion Agent | | | | | |
| Mixed-Zn-A | 2 | — | — | — | 2 |
| Mixed-Zn-B | — | 2 | — | — | — |
| Perkalink 900 | — | — | — | 1 | 1 |
| Zinc Oxide | 5 | 5 | 5 | 5 | 5 |
| Sulfur | 2.5 | 2.5 | 2.5 | 2.5 | 2.5 |
| Accelerator TBBS | 1.5 | 1.5 | 1.5 | 1.5 | 1.5 |

After mixing, each of the above recipes was and cured at 170° C. for 20, 60, and 70 minutes, then tested to obtain various data. cured at 170° C. for 20 and 60 minutes and tested to determine the following properties:

| | Test No. | | | | |
|---|---|---|---|---|---|
| | T1 | T2 | T3 | T4 | T5 |
| | Anti Reversion Agent | | | | |
| | Mixed-Zn-A | Mixed-Zn-B | none | PK900 | PK900 + Mixed-Zn-A |
| Cured at 170° C. for 20 minutes | | | | | |
| Hardness | 67.7 | 65 | 63.8 | 66.3 | 68.6 |
| 300% modulus | 14 | 14.4 | 12.1 | 12.8 | 15.1 |
| Tensile strength | 22.2 | 23.9 | 24.1 | 24.1 | 22.8 |
| Elongation at break | 426 | 447 | 505 | 483 | 413 |
| Cured at 170° C. for 60 minutes | | | | | |
| Hardness, Shore A | 64.7 | 63.5 | 62.4 | 64.7 | 69 |
| 300% modulus, MPa | 13.1 | 12.9 | 9.8 | 13.7 | 15.6 |
| Tensile strength, MPa | 21.6 | 21.9 | 22.6 | 23.4 | 20.7 |
| Elongation at break, % | 440 | 445 | 531 | 460 | 378 |
| Cured at Rheometer for 70 minutes | | | | | |
| Torque at 60 minutes, lb * in | 36.6 | 36.3 | 32.8 | 37.5 | 41.3 |
| Reversion, % | 22.1 | 23.5 | 33.3 | 16.9 | 7.8 |
| Mooney viscosity | 51.5 | 54.1 | 59.2 | 54.1 | 54.8 |
| Elastic Modulus, G' at 1 Hz, 10% strain 100° C. | 176 | 193 | 202 | 184 | 191 |

The anti reversion agent of the present invention can also be used with other anti reversion agents like Perkalink 900 of Flexsys NV to obtain better reversion properties relative to U.S. Pat. No. 5,623,007 (the relevant portions of which are incorporated herein by reference). Test No. T5 shows the results thereof.

The invention sample, test T1, compares favorably with the sample, test T2, using an anti-reversion agent made according to the method described in U.S. Pat. No. 5,302,315. Compared with the test without organic zinc_salts T3, test T1 shows higher hardness, modulus, lower Mooney viscosity, lower G' (easier to process), and lower reversion.

Example 6

Preparation of Organic Zinc Salt Coated Filler

Prepare 100 grams of zinc ammonia complex solution per Example 1 above. Add 81 grams of stearic acid to the solution and agitate. It dissolves completely. Spray the solution onto 810 grams of clay S-400 and then heat the mixture at 90° C. to dry off ammonia and carbon dioxide. Dry the mixture at 110° C. for 19 hours to reach a moisture content of 0.37%. Mill the resulting powder to 99.9% passing 325 mesh to obtain sample C-clayA. Using the same method but substituting clay S-400 with precipitated silica VN3, zinc stearate coated silica C-silicaA is obtained. The composites displayed the following properties:

|  | C-clayA | C-silicaA |
|---|---|---|
| Bulk density | 0.54 | 0.13 |
| % Zinc | 1.05 | 1.03 |
| pH | 9.38 | 8.35 |

Example 7

Preparation of Mixed Organic Zinc Salt Coated Filler

Prepare 200 grams of zinc ammonia complex solution per Example 1 above. Add 21.5 grams of benzoic acid and 64.4 grams of caprylic/capric acid blend into the solution and agitate. They dissolved completely. Spray the solution on to 945 grams of clay S-400 and then heat the mixture at 150° C. to dry off ammonia and carbon dioxide with heavy agitation for 4 hours. The mixture becomes dry with only 0.11% moisture. Mill the resulting powder to 99.9% passing 325 mesh to obtain sample C-clayB.

|  | C-clayB |
|---|---|
| Bulk density | 0.79 |
| % Zinc | 1.85 |
| pH | 8.62 |

Example 8

Preparation of Zinc Diethyldithiocarbamate

Add 73 grams of diethylamine to 150 grams of distilled water and then add 1,200 grams of 4% ammonium hydroxide solution made with distilled water and with temperature controlled at 25° C. under heavy agitation. Then add 0.2 gram of emulsifier Tanemul 1203, lower the temperature to 15° C. and add 78.5 grams of carbon disulfide slowly in the course of 1 hour, keeping the temperature below 20° C. Continue the agitation for another 4 hours at room temperature. Then add 346 grams of zinc ammonia complex solution A as in Example 1, which contains 9.56% zinc, carbon dioxide, and ammonia to the solution with heavy agitation in the course of 5 minutes. White precipitates appear, ammonia is liberated. Gradually heat the solution to 40° C. with agitation for 1 hour. The pH is of the mixture is at 10.38. Heat the solution further to boiling for 60 minutes to liberate all ammonia. Vacuum filter the precipitates, analysis shows the filtrate contains 0% of zinc and no ammonia, with a pH of 8.42. The filtration is finished in 5 minutes. Wash the solid at the filter with 500 ml of 80° C. distilled water four times. Then dry the precipitate at 110° C. for 6 hours to obtain 178 grams of 98% ZDEC with a moisture content of 0.1%. This sample is labeled ZDEC-A.

Using the same method as above but substituting 394 grams of zinc sulfate solution with 8.40% zinc for the 346 grams of zinc ammonia carbonate solution, we obtain 169 grams of zinc diethyldithiocarbamate sample ZDEC-B.

Example 9

Alternative Preparation of Zinc Diethyldithiocarbamate

The sequence of addition of the zinc compound and carbon disulfide is changed to conform to the method of Example 1 of U.S. Pat. No. 6,534,675, and zinc diethyldithiocarbamate (ZDEC-C) is prepared. Add 73 grams of diethylamine to 150 grams of water with temperature controlled at 25° C., then add 900 grams of solution with 3.4% ammonium hydroxide and 1% carbon dioxide which prevents the premature precipitation of the zinc content. Further add 346 grams of zinc ammonia complex solution A as in Example 1 containing 9.56% zinc to the solution and 1.7 grams of emulsifier Tanemul 1203. Lower the solution temperature to 15° C., add 78.5 grams of carbon disulfide slowly into the mixture under heavy agitation over 1 hour while keeping the temperature at or below 20° C. Yellowish white precipitates appear with the addition, and vapor comes out from the mixture. Continue the agitation for 3 hours, then heat the solution gradually to 40° C. Boil the solution, continue agitation for another 2 hours, then vacuum filter the precipitates. The filtrate has a pH of 8.45, and is substantially free of zinc and ammonia. The filtration is finished in 5 minutes. Wash the solid at the filter with 500 ml of 80° C. distilled water four times. Then dry the precipitate at 110° C. for 2 hours to obtain 172 grams of zinc diethyldithiocarbamate with 0.1% moisture content. We call this sample ZDEC-C.

Unlike U.S. Pat. No. 6,534,675, no caustic soda is used and no sodium sulfate is produced, yet zinc is added before carbon disulfide as proposed by that patent. Filtration is also easy in this process. If ammonia, carbon dioxide, and zinc oxide are added at a certain stage instead of the zinc ammonia carbonate complex, zinc ammonia carbonate complex can be generated in situ. This is equivalent to adding zinc ammonia carbonate complex solution.

Analysis of ZDEC samples A, B, C, and a commercial sample yields the following data:

|  | ZDEC-A | ZDEC-B | ZDEC-C | Commercial ZDEC |
|---|---|---|---|---|
| Percent zinc | 18.8 | 18.54 | 18.85 | 17.86 |
| Acid value, mg KOH/gr | 1.25 | 0.77 | 3.62 | 3.25 |
| Bulk density | 0.7 | 0.69 | 0.57 | 0.63 |
| pH of 10% slurry | 9.37 | 7.66 | 8.66 | 8.27 |
| Melting property ° C., initial/final: | 172-176 | 170-176 | 170-174 | 174-175 |
| Conductivity*, $10^{-4}$ S/m | 30 | 110 | 30 | 370 |
| Xylene insoluble, % | 0% | 0% | 0% | 3.7 |

The much lower conductivity of ZDEC-A and ZDEC-C indicate an easier wash and less water soluble matter in the zinc diethydithiocarbamate. Other zinc dithiocarbamates like zinc dimethyldithiocarbamate, zinc dibenzyldithiocarbamate, zinc dibutyldithiocarbamate or zinc ethylenebisdithiocarbamate can also be prepared using methods of Example 8 and Example 9.

Example 10

Rubber Compounds Containing Organic Zinc Salt Coated Filler

Tire tread made of natural rubber is compounded according to the following recipes and cured at 170° C. for 20 and 70 minutes to obtain various data. All units are in phr (parts per hundred parts of rubber).

|  | Test No. | | | |
| --- | --- | --- | --- | --- |
|  | T21 | T22 | T23 | T24 |
| Natural Rubber | 100 | 100 | 100 | 100 |
| Carbon Black N330 | 34.5 | 34.5 | 34.5 | 34.5 |
| Filler | | | | |
| Clay S400 | 20 | 20 | — | — |
| C-clayB | — | — | 22 | 22 |
| Silane Si69 | — | 1 | — | 1 |
| Aromatic Oil | 8 | 8 | 8 | 8 |
| Stearic Acid | 2 | 2 | 2 | 2 |
| Anti oxidant Santoflex 6PPD | 1 | 1 | 1 | 1 |
| Zinc Oxide | 4 | 4 | 4 | 4 |
| Sulfur | 2.5 | 2.5 | 2.5 | 2.5 |
| Accelerator TBBS | 1.5 | 1.5 | 1.5 | 1.5 |
| Cured at 170° C. for 20 minutes | | | | |
| Hardness | 62.1 | 64.3 | 65.2 | 66.7 |
| 300% modulus | 9.28 | 9.48 | 9.71 | 11 |
| Tensile strength | 22.8 | 23.9 | 21.9 | 23.7 |
| Elongation at break | 515 | 532 | 490 | 503 |
| Abrasion resistance, volume loss mm$^3$ | 207 | 164 | 153 | 148 |
| Cured at Rheometer for 70 minutes | | | | |
| Torque at 60 minutes, lb * in | 29.6 | 31.2 | 34.2 | 35.6 |
| Reversion, % DIN 53 529 | 31.5 | 27.1 | 21.7 | 18.9 |

The coated filler without silane performs similar to the recipe with silane alone. The recipe with both coated filler and silane performs much better in modulus, hardness, abrasion resistance and reversion resistance. Although clay is a more economic filler, high abrasion loss of rubber compound with clay is a drawback. The improvement in abrasion resistance with an organic zinc salt coating on clay, with and without silane in tests T23 and T24 relative to T21, shows the utility of the present invention for tire applications.

Example 11

Rubber Compounds Containing Organic Zinc Salts and Silane Coupling Agents

Tire tread made of natural rubber is compounded according to the following recipes and cured at 170° C. for 20 and 70 minutes to obtain various data. All units are in phr (parts per hundred parts of rubber).

|  | Test No. | | | |
| --- | --- | --- | --- | --- |
|  | T31 | T32 | T33 | T34 |
| Natural Rubber | 100 | 100 | 100 | 100 |
| Carbon Black N330 | 34.5 | 34.5 | 34.5 | 34.5 |
| Filler, silica VN3 | 17 | 17 | 17 | 17 |
| Mixed-Zn-A, | — | — | 2 | 2 |
| Silane | — | 1 | — | 1 |
| Aromatic Oil | 8 | 8 | 8 | 8 |
| Stearic Acid | 2 | 2 | 2 | 2 |
| Anti oxidant Santo flex 6PPD | 1 | 1 | 1 | 1 |
| Zinc Oxide | 4 | 4 | 4 | 4 |
| Sulfur | 2.5 | 2.5 | 2.5 | 2.5 |
| Accelerator TBBS | 1.5 | 1.5 | 1.5 | 1.5 |
| Cured at 170° C. for 20 minutes | | | | |
| Hardness, shore A | 54.3 | 57.8 | 60.5 | 62.9 |
| 100% modulus MPa | 1.31 | 1.61 | 1.91 | 2.32 |
| 300% modulus MPa | 5.91 | 7.71 | 8.68 | 11.05 |
| Tensile strength MPa | 21.8 | 22.9 | 22.5 | 21.1 |
| Elongation at break % | 665 | 611 | 549 | 471 |
| Abrasion resistance, volume loss mm$^3$ | 206 | 151 | 154 | 139 |
| Mooney viscosity, ML1 + 4@ 100° C. | 45.2 | 41.5 | 37.1 | 38.1 |
| Heat buildup, C | 21.5 | 16.5 | 16.5 | 16.5 |
| Cured at 170° C. for 60 minutes | | | | |
| Abrasion resistance, volume loss mm$^3$ | 242 | 164 | 160 | 149 |
| Cured at Rheometer for 70 minutes | | | | |
| Torque at 60 minutes, lb * in | 26.3 | 28.5 | 32.1 | 35 |
| Reversion, % DIN 53 529 | 40.1 | 35.2 | 23.5 | 19 |

The combination of silane and mixed organic zinc salts in test T34 dramatically increases the hardness, modulus, reversion resistance of the compound. The abrasion resistance of over-cured compound at 60 minutes cure is also increased markedly compared with samples using either silane or organic zinc salts alone. As for samples using silane alone or organic zinc salts alone (T32 and T33), organic zinc salts give comparable result to silane coupling agent. The Mooney viscosity of the tests with organic zinc salts is also lower, indicating easier processing of the rubber compound. The lower heat buildup in test T32, T33, and T34 indicates lower hysteresis and lower rolling resistance for tires.

Example 12

Using Organic Zinc Salts With Fillers and Silane Coupling Agent in Mixed Synthetic Rubber and Natural Rubber Compounds Tire tread made of SBR and natural rubber is compounded according to the following recipes and cured at 170° C. for 20 and 70 minutes to obtain various data. All units are in phr (parts per hundred parts of rubber.)

|  | Test No. | | |
| --- | --- | --- | --- |
|  | T41 | T42 | T43 |
| Filler No. | Silica | C-silicaA | C-silicaA |
| Natural Rubber | 65 | 65 | 65 |
| SBR | 35 | 35 | 35 |
| Carbon Black N330 | 48.5 | 48.5 | 48.5 |
| Filler, silica VN3 | 17 | — | — |
| C-silicaA | — | 19 | 19 |
| Silane | 1 | — | 1 |
| Aromatic Oil | 8 | 8 | 8 |
| Stearic Acid | 2 | 2 | 2 |
| Anti oxidant Santo flex 6PPD | 1 | 1 | 1 |
| Zinc Oxide | 4 | 4 | 4 |

-continued

|  | Test No. | | |
|---|---|---|---|
|  | T41 | T42 | T43 |
| Sulfur | 2.5 | 2.5 | 2.5 |
| Accelerator TBBS | 1.5 | 1.5 | 1.5 |
| Cured at 170° C. for 20 minutes | | | |
| Hardness, shore A | 72.9 | 71.5 | 75.3 |
| 100% modulus, MPa | 3.7 | 3.67 | 4.48 |
| 300% modulus, MPa | 14.79 | 14.08 | 16.63 |
| Tensile strength, MPa | 18.38 | 18.12 | 18.76 |
| Elongation at break, % | 369 | 375 | 338 |
| Abrasion resistance, volume loss mm$^3$ | 171 | 172 | 154 |
| Cured at Rheometer for 70 minutes | | | |
| Torque at 60 minutes, lb * in | 44.6 | 45.1 | 47.5 |
| Reversion, % DIN 53 529 | 15.3 | 12.7 | 10.1 |

Like the natural rubber tire tread compound above, the compound with silane alone performs similar to the one with mixed organic zinc salts, while the combination of silane and organic zinc salts increases the hardness, modulus, reversion resistance of the compound. The improved reversion resistance is important for large and thick rubber parts, as their cure times are usually much longer.

Example 13

Using Zinc 2-Mercaptobenzothiazole as an Accelerator in a Shoe Rubber Formulation Shoe sole made of SBR and natural rubber is compounded according to the following recipes and cured at 150° C. for 8 minutes to obtain various data. All units are in phr (parts per hundred parts of rubber).

| Parts by weight | Test No. | | | |
|---|---|---|---|---|
|  | T51 | T52 | T53 | T54 |
| Standard Thai Rubber STR-5L | 50 | 50 | 50 | 50 |
| BR 01 | 50 | 50 | 50 | 50 |
| Stearic acid | 1 | 1 | 1 | 1 |
| BHT | 1.5 | 1.5 | 1.5 | 1.5 |
| Paraffin wax | 1 | 1 | 1 | 1 |
| Paraffin oil | 10 | 10 | 10 | 10 |
| Silica, Hilsil 255 | 50 | 50 | 50 | 50 |
| PEG 4000 | 3 | 3 | 3 | 3 |
| Zinc oxide | 4 | 4 | 4 | 4 |
| Accelerator TMTD | 0.7 | 0.7 | 0.7 | 0.7 |
| Accelerator MBTS | 0.5 | 0.5 | 0.5 | 0.5 |
| Accelerator MBT | 1 | — | — | — |
| Accelerator ZMBT-A | — | 1 | — | — |
| Accelerator ZMBT-B | — | — | 1 | — |
| Accelerator ZMBT, commercial | — | — | — | 1 |
| Sulfur | 2 | 2 | 2 | 2 |

The compound is cured at 150° C. for 8 minutes with the following property:

|  | Test No. | | | |
|---|---|---|---|---|
|  | T51 | T52 | T53 | T54 |
| Hardness | 67.5 | 67.8 | 67.5 | 68.2 |
| 300% modulus | 6.11 | 5.89 | 6.42 | 6.03 |

-continued

|  | Test No. | | | |
|---|---|---|---|---|
|  | T51 | T52 | T53 | T54 |
| Tensile strength MPa | 14.91 | 16.45 | 16.86 | 16.88 |
| Elongation at break, % | 536 | 597 | 554 | 581 |
| Rheometer Data, 150° C., 10 minutes: | | | | |
| Minimum torque lb * in | 26.5 | 22.9 | 24 | 23.7 |
| Maximum torque lb * in | 59 | 61.4 | 59.1 | 59.4 |
| Scorch time, ts2 min | 0:30 | 1:40 | 1:08 | 1:51 |
| Cure time, tc90 min | 1:16 | 2:25 | 1:49 | 2:26 |

As expected, zinc 2-mercaptobenzothiazole (T52, T53 and T54) gives the same property as MBT (T51) in dry rubber goods, but dramatically increases the scorch time of the rubber compound compared with fast cure MBT while cure time is also increased. The longer scorch time is sometimes needed to allow a rubber compound more time to "flow" inside a mould for better product quality. If scorch time is too short, rubber compound may not be able to fully fill up the mould, resulting in an inferior product.

Example 14

Using Zinc Diethyldithiocarbamate as a Secondary Accelerator in a Tire Tread Formulation Tire tread made of natural rubber is compounded according to the following recipes at the following and cured at 170° C. for 20, 60, and 70 minutes to obtain various data. All units are in phr (parts per hundred parts of rubber.)

|  | Test No. | | | | |
|---|---|---|---|---|---|
|  | T61 | T62 | T63 | T64 | T65 |
| Natural Rubber | 100 | 100 | 100 | 100 | 100 |
| Carbon Black N330 | 48.5 | 48.5 | 48.5 | 48.5 | 48.5 |
| Aromatic Oil | 8 | 8 | 8 | 8 | 8 |
| Stearic Acid | 2 | 2 | 2 | 2 | 2 |
| Anti oxidant Santo flex 6PPD | 1 | 1 | 1 | 1 | 1 |
| Zinc Oxide | 4 | 4 | 4 | 4 | 4 |
| Accelerator TBBS | 1.1 | 1.1 | 1.1 | 1.1 | 1.1 |
| Accelerator TMTD | 0.4 | — | — | — | — |
| ZDEC-A R427 | — | 0.4 | — | — | — |
| ZDEC-B R438 | — | — | 0.4 | — | — |
| ZDEC-C R433 | — | — | — | 0.4 | — |
| ZDEC-commercial R406 | — | — | — | — | 0.4 |
| Sulfur | 2.5 | 2.5 | 2.5 | 2.5 | 2.5 |
| Cured at 170° C. 20 minutes | | | | | |
| Hardness | 65.8 | 63.1 | 63.4 | 62.4 | 60.1 |
| 300% modulus | 12.7 | 11.7 | 12 | 12.8 | 13 |
| Tensile strength MPa | 22.5 | 23.1 | 23.7 | 25.1 | 23.1 |
| Elongation at break, % | 450 | 479 | 485 | 489 | 461 |
| Rheometer Data, 170° C., 70 minutes: | | | | | |
| Minimum torque, lb * in | 9.2 | 9.8 | 10.2 | 9.8 | 9.7 |
| Maximum torque, lb * in | 46 | 44.1 | 45.2 | 43.9 | 43.6 |
| Scorch time, ts2 min | 1.16 | 0.97 | 0.98 | 0.96 | 0.96 |
| Cure time, tc90 min | 1.84 | 1.64 | 1.67 | 1.64 | 1.64 |
| Reversion, % | 24.5 | 31.5 | 36.8 | 34.4 | 38.6 |

The property of the rubber compound using commercial zinc diethyldithiocarbamate is the same as the property of various compounds using zinc diethyldithiocarbamate prepared by this invention.

CONCLUSION/SUMMARY

Thus, the invention concerns organic zinc salts and/or organic zinc salt coated particles, methods of coating particles with organic zinc salts, and various applications of such coated particles, including applications in rubber, other polymer materials, and pesticides and/or fungicides. As compared to rubber formulations including organic zinc salts and/or filler particles alone, formulations including the present coated particles may have a lower Mooney viscosity and lower minimum torque, improved dispersability, a higher modulus at 100% and/or at 300% elongation, a higher tensile strength, better aging resistance, better abrasion resistance, lower density, and/or lower heat build up. Thus, products containing the present organic zinc salts and/or organic zinc salt coated particles may enjoy similar or better properties than comparative products that include a conventional filler and/or organic zinc salts per se, and the present coated particles may result in cost savings for the corresponding product formulations.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A method for preparing an organic zinc salt, comprising:
   a) mixing an aqueous zinc ammonia carbonate complex solution with one or more organic acids and/or soluble organic acid salts to form an aqueous mixture;
   b) agitating, and optionally heating, the aqueous mixture to at least partially remove ammonia and carbon dioxide from the aqueous mixture, thereby forming said organic zinc salt in water;
   c) optionally, cooling the organic zinc salt in the water to a temperature of from about 5° C. to 30° C.;
   d) filtering the organic zinc salt to isolate said organic zinc salt;
   e) optionally, washing the isolated organic zinc salt;
   f) drying the isolated organic zinc salt; and
   g) optionally, milling the isolated organic zinc alt.

2. The method of claim 1, further comprising preparing the zinc ammonia carbonate complex from (i) a zinc source, (ii) an ammonia source and a carbon dioxide source, wherein said zinc ammonia carbonate complex solution contains zinc in a concentration of from about 1% to 15% by weight, ammonia in a concentration of from 1% to 20% by weight, and carbon dioxide in a concentration of from 0 to 10% by weight.

3. The method of claim 2, wherein the zinc source is selected from the group consisting of zinc oxide, zinc carbonate, electric arc furnace dust and zinc ash.

4. The method of claim 1, wherein the one or more organic acids and/or salts thereof consist essentially of a salt of an organic acid, and the method further comprises preparing said salt of said organic acid by reacting said organic acid with sodium hydroxide, potassium hydroxide, or an ammonium hydroxide.

5. The method of claim 1, wherein step (b) further comprises heating the aqueous mixture at a temperature of from about 40° C. to 150° C.

6. The method of claim 1, wherein said isolated organic zinc salt is insoluble or sparingly soluble in water.

7. The method of claim 1, wherein said one or more organic acids are selected from the group consisting of $C_7$-$C_{24}$ aliphatic carboxylic acids, aromatic carboxylic acids, and 2-mercaptobenzothiazole.

8. The method of claim 7, wherein said one or more organic acids comprises a mixture of one or more $C_7$-$C_{24}$ aliphatic carboxylic acids and one or more aromatic carboxylic acids.

9. The method of claim 1, comprising drying the isolated organic zinc salt at a temperature of from about 50° C. to 200° C.

10. The method of claim 1, wherein mixing said zinc ammonia carbonate complex solution with said one or more organic acids further comprises generating said one or more organic acids in situ.

11. The method of claim 10, wherein mixing said zinc ammonia carbonate complex solution with said one or more organic acids and generating said one or more organic acids in situ comprises:
   a) dissolving an amine in water;
   b) adding an ammonium hydroxide solution to form a second solution;
   c) adding the zinc ammonia carbonate complex or a solution thereof to the second solution;
   d) optionally, adding one or more emulsifiers; and
   e) adding carbon disulfide at a temperature of less than 40° C. to form a mixture and agitating the mixture to precipitate the organic zinc salt.

12. The method of claim 11, wherein said ammonium hydroxide solution comprises ammonium hydroxide in an amount of from about 1% to 10% by weight.

13. The method of claim 11, comprising adding said zinc ammonia carbonate complex or solution thereof to said second solution after adding said carbon disulfide.

14. The method of claim 11, wherein adding said zinc ammonia carbonate complex or solution thereof comprises adding a zinc source, ammonia, and optionally carbon dioxide to form said zinc ammonia carbonate complex.

15. The method of claim 11, wherein said amine comprises a disubstituted amine selected from the group consisting of dialkylamines, diarylamines, diaralkylamines, and ethylene diamine.

16. The method of claim 15, wherein said amine is selected from the group consisting of dimethylamine, diethylamine, dibenzylamine, dibutylamine and ethylenediamine, and said organic zinc salt is selected from the group consisting of zinc dimethyldithiocarbamate, zinc diethyldithiocarbamate, zinc dibenzyldithiocarbamate, zinc dibutyldithiocarbamate and zinc ethylenebisdithiocarbamate.

17. The method of claim 1, further comprising heating the aqueous mixture to at least partially remove ammonia and carbon dioxide from the aqueous mixture, thereby forming said organic zinc salt.

18. The method of claim 17, further comprising cooling the aqueous mixture to a temperature of from about 5° C. to 30° C. prior to filtering the aqueous mixture to isolate said organic zinc salt.

19. The method of claim 1, further comprising washing the isolated organic zinc salt.

20. The method of claim 1, further comprising milling the isolated organic zinc salt.

21. The method of claim 1, wherein the aqueous mixture is formed by mixing said aqueous zinc ammonia carbonate complex solution with at least one organic acid.

22. The method of claim 1, wherein the mixture is formed by mixing said aqueous zinc ammonia carbonate complex solution with at least one soluble organic acid salt.

23. The method of claim 2, wherein said ammonia source comprises ammonia or ammonium hydroxide.

24. The method of claim 2, wherein said carbon dioxide source comprises carbon dioxide.

25. The method of claim 1, wherein said one or more organic acids comprises a dithiocarbamic acid.

26. The method of claim 25, wherein generating said dithiocarbamic acid comprises:
   a) dissolving an amine in water;
   b) adding an ammonium hydroxide solution to form a second solution; and
   c) adding carbon disulfide.

27. The method of claim 26, wherein generating said one or more organic acids in situ comprises:
   a) adding said zinc ammonia carbonate complex or solution thereof to the second solution; and
   b) after adding said carbon disulfide, agitating the mixture to precipitate the organic zinc salt.

28. The method of claim 26, wherein said carbon disulfide is added at a temperature of less than 40° C.

29. The method of claim 11, comprising adding said one or more emulsifiers.

30. The method of claim 11, wherein said zinc ammonia carbonate complex or solution thereof is added to the second solution prior to adding said carbon disulfide.

31. The method of claim 11, wherein said carbon disulfide is added to the second solution prior to adding said zinc ammonia carbonate complex or solution thereof.

32. The method of claim 4, further comprising preparing said salt of said organic acid by reacting said organic acid with said ammonium hydroxide.

33. The method of claim 7, wherein said one or more organic acids comprises one or more of said $C_7$-$C_{24}$ aliphatic carboxylic acids.

* * * * *